(12) United States Patent
Miao et al.

(10) Patent No.: US 10,621,738 B2
(45) Date of Patent: Apr. 14, 2020

(54) 2D/3D REGISTRATION FOR ABDOMINAL AORTIC ANEURYSM INTERVENTION

(75) Inventors: Shun Miao, Plainsboro, NJ (US); Rui Liao, Princeton Junction, NJ (US); Marcus Pfister, Bubenreuth (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 13/398,999

(22) Filed: Feb. 17, 2012

(65) Prior Publication Data

US 2020/0051258 A1   Feb. 13, 2020

Related U.S. Application Data

(60) Provisional application No. 61/453,177, filed on Mar. 16, 2011.

(51) Int. Cl.
*G06T 7/38* (2017.01)
*A61B 6/00* (2006.01)
*G06K 9/00* (2006.01)
*G06T 7/00* (2017.01)

(52) U.S. Cl.
CPC ............ *G06T 7/38* (2017.01); *A61B 6/504* (2013.01); *G06K 9/00214* (2013.01); *G06T 7/0012* (2013.01); *G06T 2207/10081* (2013.01); *G06T 2207/30101* (2013.01)

(58) Field of Classification Search
None
See application file for complete search history.

(56) References Cited

U.S. PATENT DOCUMENTS

| | | | | |
|---|---|---|---|---|
| 6,711,433 B1* | 3/2004 | Geiger | ................. | A61B 6/463 378/42 |
| 6,721,590 B2* | 4/2004 | Ohishi | ................. | A61B 6/466 600/425 |
| 8,126,239 B2* | 2/2012 | Sun | ........................ | A61B 6/12 382/131 |
| 8,252,049 B2* | 8/2012 | Maschke | ................ | A61B 6/12 606/108 |

(Continued)

OTHER PUBLICATIONS

Brown, Louise C., and Janet T. Powell. "Risk factors for aneurysm rupture in patients kept under ultrasound surveillance." Annals of surgery 230.3 (1999): p. 289.

(Continued)

*Primary Examiner* — Anand P Bhatnagar

(57) ABSTRACT

A method for performing 2D/3D registration includes acquiring a 3D image. A pre-contrast 2D image is acquired. A sequence of post-contrast 2D images is acquired. A 2D image is acquired from a second view. The first view pre-contrast 2D image is subtracted from each of the first view post-contrast 2D images to produce a set of subtraction images. An MO image is generated from the subtraction images. A 2D/3D registration result is generated by optimizing a measure of similarity between a first synthetic 2D image and the MO image and a measure of similarity between a second synthetic image and the intra-operative 2D image from the second view by iteratively adjusting an approximation of the pose of the patient in the synthetic images and iterating the synthetic images using the adjusted approximation of the pose.

21 Claims, 4 Drawing Sheets

(56) References Cited

U.S. PATENT DOCUMENTS

| | | | | |
|---|---|---|---|---|
| 8,594,274 | B2* | 11/2013 | Hoernig | A61B 6/025 378/22 |
| 8,675,996 | B2* | 3/2014 | Liao | G06T 7/33 382/128 |
| 2006/0023840 | A1* | 2/2006 | Boese | A61B 6/12 378/98.12 |
| 2006/0036167 | A1* | 2/2006 | Shina | A61B 6/12 600/433 |
| 2008/0095421 | A1* | 4/2008 | Sun | A61B 6/12 382/131 |
| 2011/0069063 | A1* | 3/2011 | Liao | A61B 6/5235 345/419 |
| 2012/0022366 | A1* | 1/2012 | Pfister | A61B 6/032 600/427 |
| 2013/0089251 | A1* | 4/2013 | Ohishi | A61B 6/481 382/131 |

OTHER PUBLICATIONS

Bansal, Ravi, et al. "Entropy-based, multiple-portal-to-3dct registration for prostate radiotherapy using iteratively estimated segmentation." International Conference on Medical Image Computing and Computer-Assisted Intervention. Springer, Berlin, Heidelberg, 1999; pp. 567-578.

Viola, et al.; "Alignment by maximization of mutual information"; Proceedings of IEEE International Conference on Computer Vision; 1995; pp. 16-23.

Khamene, Ali, et al. "Automatic registration of portal images and volumetric CT for patient positioning in radiation therapy." Medical image analysis 10.1 (2006): 96-112.

Palégyi, et al; ". A sequential 3D thinning algorithm and its medical applications"; (Jun. 2001). In Biennial International Conference on Information Processing in Medical Imaging (pp. 409-415); Springer, Berlin, Heidelberg.

Liao; "2-D/3-D registration of C-arm CT volumes with fluoroscopic images by spines for patient movement correction during electrophysiology." In 2010 IEEE International Symposium on Biomedical Imaging: From Nano to Macro, pp. 1213-1216. IEEE, 2010.

Lombaert, H., et al.; "A multilevel banded graph cuts method for fast image segmentation"; Oct. 2005; In Tenth IEEE International Conference on Computer Vision (ICCV'05) vol. 1 (vol. 1, pp. 259-265). IEEE.

Perona, Pietro, et al.; "Scale-space and edge detection using anisotropic diffusion." IEEE Transactions on pattern analysis and machine intelligence 12.7 (1990): 629-639.

* cited by examiner

2D/3D REGISTRATION FOR ABDOMINAL AORTIC ANEURYSM INTERVENTION

CROSS-REFERENCE TO RELATED APPLICATION

The present application is based on provisional application Ser. No. 61/453,177, filed Mar. 16, 2011, the entire contents of which are herein incorporated by reference.

TECHNICAL FIELD

The present disclosure relates to two-dimensional (2D)/three-dimensional (3D) registration and, more specifically, to 2D/3D registration for abdominal aortic aneurysm intervention.

DISCUSSION OF THE RELATED ART

Abdominal aortic aneurysm (AAA) is a localized dilation (ballooning) of the abdominal aorta. There is a risk of rupture of the aneurysm if the expansion becomes large enough. The mortality rate for AAA rupture is up to 90%. Conventional treatment for AAA involves open invasive surgery in which the surgeon opens the abdomen and stitches in a replacement section of artery. Modern treatments for AAA may involve endovascular repair. In endovascular repair, a stent graft may be brought into place through the arteries. Such intervention may rely heavily on radiographic guidance, such as a series of two-dimensional X-ray images acquired in real-time using a fluoroscope. Suitable visualization may be procured by repeatedly injecting a radiocontrast agent into the arteries.

X-ray fluoroscopy and repeated injection of radiocontrast may expose the patient to a higher-than-desired dose of radiation. However, suitable visualization of the abdominal aorta using X-ray fluoroscopy may rely upon the continued use of radiocontrast.

SUMMARY

A method for performing 2D/3D registration includes acquiring a pre-operative 3D image of a patient. An intra-operative pre-contrast 2D image of the patient is acquired from a first view. A radiocontrast agent is administered to the patient. A sequence of intra-operative post-contrast 2D images is acquired of the patient from the first view. An intra-operative 2D image of the patient is acquired of the patient from a second view that is acquired at a different angle with respect to the patient than the first view. The first view pre-contrast 2D image is subtracted from each of the first view post-contrast 2D images to produce a set of first view subtraction images. A maximum opacity (MO) image is generated from the set of first view subtraction images. A first synthetic 2D view is generated from the pre-operative 3D image that approximates the first view based on an initial approximation of an intra-operative pose of the patient. A second synthetic 2D view is generated from the pre-operative 3D image that approximates the second view based on the initial approximation of the intra-operative pose of the patient. A 2D/3D registration result is generated by optimizing a measure of similarity between the first synthetic 2D view and the MO image and a measure of similarity between the second synthetic image and the intra-operative 2D image of the patient from the second view by iteratively adjusting the approximation of the pose of the patient and iterating the first and second synthetic 2D views using the adjusted approximation of the pose of the patient.

The method may further include acquiring real-time 2D images of the patient and using the generated 2D/3D registration result to register subsequent 2D images to the 3D image.

The measure of similarity between the first synthetic 2D view and the MO image may be bases on visualization of an aorta and the measure of similarity between the second synthetic 2D view and the intra-operative 2D image of the patient from the second view is based on visualization of a spine.

Optimizing a measure of similarity between the first synthetic 2D view and the MO image and a measure of similarity between the second synthetic 2D image and the intra-operative 2D image of the patient from the second view may include estimating an on-table-plane translation and rotation by optimizing Euclidean transformation parameters to maximize a measure of similarity between the first synthetic 2D view and the MO image, estimating a table depth by maximizing a measure of similarity between the second synthetic 2D image and the intra-operative 2D image of the patient from the second view by local exhaust search, refining the table depth by optimizing the Euclidean transformation parameters to maximize a measure of similarity between the second synthetic 2D image and the intra-operative 2D image of the patient from the second view, refining an abdominal 2D/3D overlay by optimizing Euclidean transformation parameters to maximize a measure of similarity between the first synthetic 2D view and the MO image while keep a 2D/3D overlay of spine in the second view unaffected, and using a final pose yielded by a final pose refining procedure as a 2D/3D registration result.

The Euclidean transformation parameters optimized in estimating the on-table-plane translation and rotation may include two dimensions of in-table-plane translation and one dimension of in-table-plane rotation and the local exhaust search may be performed in two directions: head-foot, and table depth.

The pre-operative 3D image may be manually bridged into 15 mm capture range of a target position.

There may be no observable contrast in the intra-operative 2D image of the patient from the second view.

The pre-operative 3D image may be a computed tomography (CT) scan. The first view may be an anteroposterior view. The second view may be acquired at an angle that differs from the angle of the first view by 20 to 160 degrees, or more particularly, 40 to 60 degrees, or, for example, 50 degrees.

The intra-operative pre-contrast 2D image, the sequence of intra-operative post-contrast 2D images of the patient from the first view, and the intra-operative 2D image of the patient from a second view may each be X-ray images.

The intra-operative pre-contrast 2D image, the sequence of intra-operative post-contrast 2D images of the patient from the first view, and the intra-operative 2D image of the patient from a second view may each be acquired using an X-ray imager mounted to a C-arm. The angle of the C-arm may be changed from the angle of the first view to the angle of the second view between the acquisition of the sequence of intra-operative post-contrast 2D images of the patient from the first view and the acquisition of the intra-operative 2D image of the patient from a second view.

Subtracting the first view pre-contrast 2D image from each of the first view post-contrast 2D images to produce a set of first view subtraction images may include performing digital subtracted angiography (DSA).

Generating the MO image from the set of first view subtraction images may include generating a composite image in which each pixel of the composite image is taken as a corresponding pixel having a maximum opacity out of among the first view subtraction images. Generating the MO image from the set of first view subtraction images may include performing an anisotropic diffusion process. The spine may be segmented from the intra-operative 2D image of the patient from a second view A method for performing 2D/3D registration includes acquiring a pre-operative 3D image of a patient. A first intra-operative 2D image is acquired of the patient from a first view using contrast. A second intra-operative 2D image is acquired of the patient from a second view without using contrast. The second view is at a different angle with respect to the patient than the first view. A first synthetic 2D view is generated from the pre-operative 3D image to approximate the first view based on an initial approximation of an intra-operative pose of the patient. A second synthetic 2D view is generated from the pre-operative 3D image to approximate the second view based on the initial approximation of the intra-operative pose of the patient. A measure of similarity between the first synthetic 2D view and the first intra-operative 2D image is optimized and a measure of similarity between the second synthetic image and the second intra-operative 2D image is optimized by iteratively adjusting the approximation of the pose of the patient and iterating the first and second synthetic 2D views using the adjusted approximation of the pose of the patient. The final iteration of the first and second synthetic 2D views is used to register subsequent 2D images to the 3D image.

A method for performing 2D/3D registration includes acquiring a 3D image of a patient. A first 2D image of the patient is acquired with contrast. A second 2D image is acquired without contrast. A spine is identified from the second 2D image of the patient. A 2D/3D overlay is generated by optimizing a measure of similarity between the first 2D image and the 3D image based on the aorta and by optimizing a measure of similarity between the second 2D image and the 3D image based on the spine.

Optimizing the measure of similarity between the first 2D image and the 3D image may include estimating an on-table-plane translation and rotation by optimizing Euclidean transformation parameters to maximize a measure of similarity between the first 2D image and a first synthetic image of the 3D image, estimating the table depth by optimizing the Euclidean transformation parameters to maximize a measure of similarity between the second 2D image and the second synthetic image of the 3D image, refining the 2D/3D overlay by optimizing Euclidean transformation parameters to maximize a measure of similarity between the first 2D image and the first synthetic image of the 3D image, and using a final pose yielded by a final pose refining procedure as a 2D/3D registration result.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
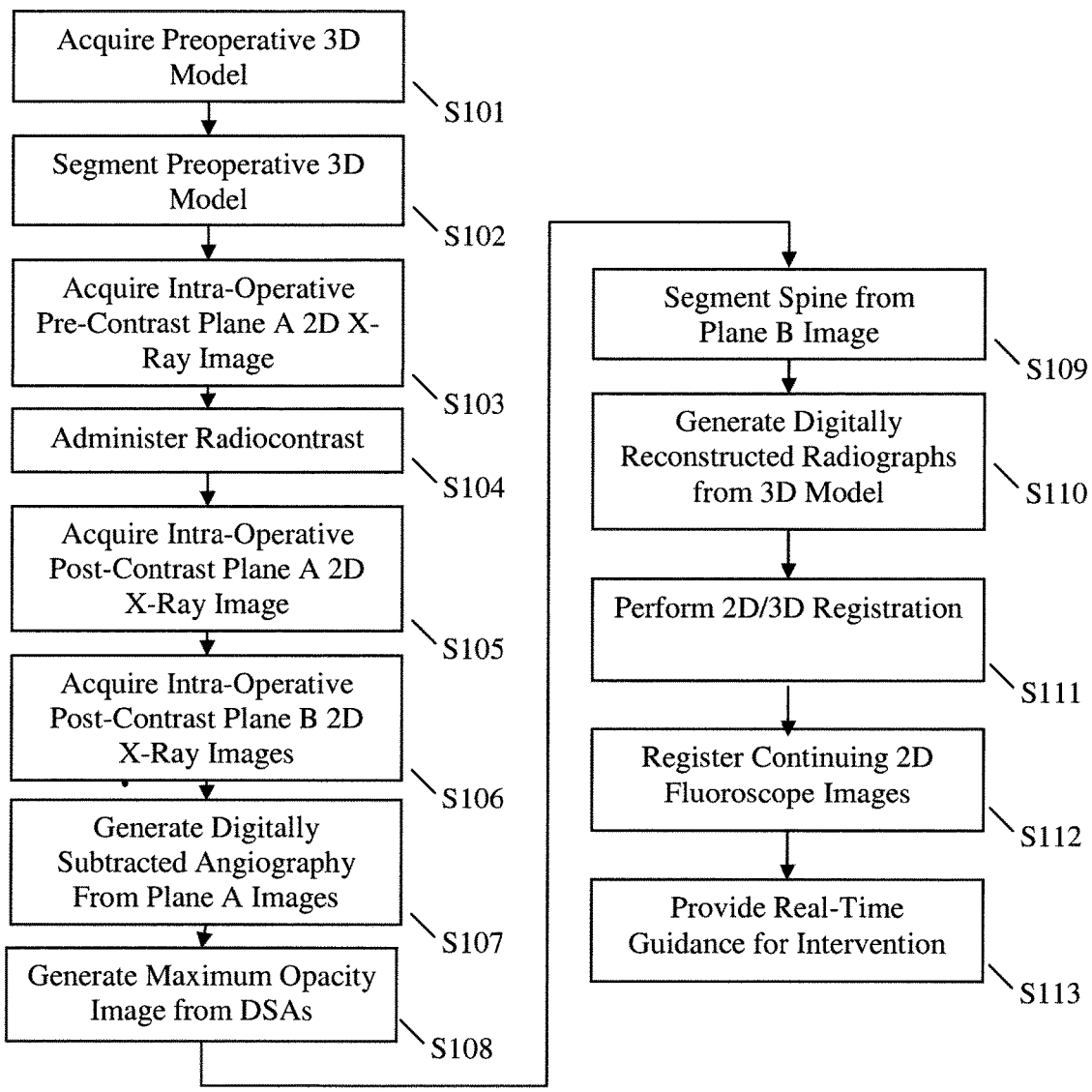
FIG. 1 is a flowchart illustrating a method for performing 2D/3D registration according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide high-detail radiographic visualization of arteries such as the abdominal aorta during interventional procedures such as endovascular aneurysm repair (EVAR) while minimizing administration of radiocontrast and minimizing exposure to ionizing radiation.

Exemplary embodiments of the present invention seek to combine structural detail from a pre-operative 3D model, for example, acquired using a magnetic resonance (MR) imager, with intra-operative 2D X-ray images. Combination of the pre-operative model with the intra-operative images may utilize 2D/3D registration in 3D space. The 2D X-ray images may be taken from multiple angles, for example, using a C-arm mounted X-ray imager. However, exemplary embodiments of the present invention may utilize an approach for image registration that may only require that contrast be injected once. The radiocontrast may be injected, for example, prior to one 2D X-ray image acquisition sequence from one angle. Subsequent 2D X-ray image acquisitions may then be performed without the injection of additional radiocontrast thereby limiting the patient's exposure while maintaining high-detail radiographic imaging for use in intervention guidance.

FIG. 1 is a flowchart illustrating a method for performing 2D/3D registration according to an exemplary embodiment of the present invention. First, a pre-operative 3D model is acquired (Step S101). The 3D model may be acquired, for example, using an MR imager or a computed tomography (CT) scanner. However, exemplary embodiments of the present invention will be described herein as using a CT scanner to acquire the 3D model. After the 3D model has been acquired, the 3D model may be segmented (Step S102). Segmentation of the 3D model may be automatic; however, manual assistance may be used. Segmentation of the 3D model may include, for example, a segmentation of the abdominal aorta and the iliac arteries. A graph-cut based segmentation method may be used for this purpose. Segmentation of the aorta may result in the generation of a segmentation mask.

The spine may also be automatically segmented from the CT volume. The spine may be segmented as a relatively course region of volume (ROV) as high accuracy may not be required of spine segmentation owing to the high degree of opacity of the spine. To obtain the ROV around the spine, the aorta segmentation mask may be used owing to the anatomical relationship by which the spine is roughly behind the abdominal aorta. In particular, with the aorta segmentation mask, the boundary of the bounding box of the aorta may be calculate for each slice of the CT volume and then dilated within the slice to both posterior and left-right directions by a certain size to obtain the spine bounding box of the aorta. Pixels belonging to the abdominal aorta may be excluded from the spine segmentation mask.

Once the patient is in the operating theatre, a first 2D X-ray image may be acquired (Step S103). This image may be acquired prior to injection of contrast into the patient's arteries. Accordingly, the image may be considered a pre-contrast image. The pre-contrast 2D X-ray image may be acquired intra-operatively. The pre-contrast 2D X-ray image may be acquired, for example, using an X-ray imager mounted to a C-arm to achieve a desired angle of acquisition. The X-ray imager may be a fluoroscope capable of taking a series of images in real-time. For acquiring this image, the X-ray imager may be angled to acquire the image in an anteroposterior view. The plane of image acquisition may be referred to herein as the "Plane A." Accordingly, the resulting image taken from this view may be called the Plane A image or the aorta image, as the view of this image may be used as a basis for matching the 3D volume.

After the first anteroposterior image is acquired, the radiocontrast may be injected (Step S104) and a sequence of one or more post-contrast X-rays may be acquired from the anteroposterior view (Step S105). This post-contrast plane A image sequence may clearly show the aorta owing to the presence of the radiocontrast agent. However, after the acquisition of this image sequence, there may no longer be sufficient radiocontrast within the patient to affect imaging. However, rather than to administer one or more additional doses of radiocontrast, exemplary embodiments of the present invention seek to perform accurate 2D/3D registration without further administration of contrast.

The C-arm may thereafter be repositioned to a second angle that is, for example, 50 degrees from the anteroposterior view and a second sequence of one or more images may be acquired (Step S106). This second sequence may be acquired without administration of additional contrast and at the time of the second sequence acquisition, there may be no observable contrast remaining in the X-ray field of view. The second sequence of images acquired at the second angle may be referred to herein as the spine image(s) or the Plane B image(s). The plane B image may be a "native X-ray image" as opposed to a subtraction image generated by subtracting one image from another image. Both the post-contrast Plane A images and the Plane B images may be acquired intra-operatively.

In the fluoroscopic post-contrast images, the image obtained may include overlaying anatomical structures in addition to the vessels of interest. To remove these distracting structures and achieve better vessel visibility, digital subtracted angiography (DSA) may be used on the Plane A images (Step S107). To perform DSA, each of the post-contrast Plane A images may be subtracted by the pre-contrast Plane A image acquired in step S103. For example, the DSA image S may be calculated from each post contrast Plane A image I and the pre-contrast Plane A image $I_0$ in accordance with the formula: $S=i-i_0$.

As the contrast medium flows through the abdominal aorta to the iliac arteries, a single DSA, which may show only a part of the vessel in each frame, may not display the complete abdominal aorta. In order to combine all the DSAs to provide a complete shape of the abdominal aorta, the minimum value of each pixel across the whole DSA sequence may be computed. A Maximum Opacity (MO) image may then be generated from the minimum pixel values (Step S108), for example, in accordance with the formula:

$$I^A = AD\left(\min_j S^j(x, y)\right) \quad (1)$$

where AD(•) denotes an anisotropic diffusion process to reduce the noise without blurring the edges.

Next, the spine may be segmented from the Plane B image(s) (Step S109). Segmentation of the spine may include generation of a 2D spine registration mask. However, as X-ray images may contain irrelevant structure and noise, which is referred to herein as outlier, to reduce the impact from outliers, the 2D spine registration mask may be generated to only include the edge of vertebrae, which is the most distinct feature of spine in spine X-ray images. Since the spine is close to being vertical in the 2D X-ray image from the typical C-Arm angulations used during AAA procedures, a steerable filter, for example, a Gabor filter, may be used to select horizontal edges:

$$G(x, y, \lambda, \theta, \sigma, \gamma) = \exp\left(-\frac{x'^2 + \gamma^2 y'^2}{2\sigma^2}\right)\sin\left(2\pi\frac{x'}{\lambda}\right) \quad (2)$$

where $$x' = x\cos(\theta) + y\sin(\theta)$$

and $$y' = -x\sin(\theta) + y\cos(\theta)$$

Here, λ may represent the wavelength of the sinusoidal factor, θ may represent the orientation of the normal to the parallel stripes of a Gabor function, σ may be the sigma of the Gaussian envelope, and γ may be the spatial aspect ratio and may specify the ellipticity of the support of the Gabor function. The parameter λ, σ and γ may be tuned to make the shape and size of the Gabor filter fit the vertebrae. Considering the fact that a large value is yielded when a Gabor filter is applied on an edge with the same orientation, eleven Gabor filters may be generated with roughly horizontal orientations $\theta_k$=80, 82°, . . . , 98°, 100° to detect vertebrae.

Each Gabor filter may be applied on the spine image as an edge detector by computing the convolution:

$$E_k = G(x,y,\lambda,\theta_k,\sigma,\gamma)*I^S \quad (3)$$

The maximum value of each pixel yielded by the 11 Gabor filters is selected:

$$E(x, y) = \max_k E_k(x, y) \quad (4)$$

The pixels above a particular threshold, for example, 85% of the histogram of E(x,y), may be classified as vertebrae points and the spine mask may be generated accordingly. To eliminate the edges caused by noise and irrelevant structures, Connected Components Analysis may be further applied to the spine mask to remove those isolated components smaller than a predetermined size, for example, 80 pixels. The generated spine mask is denoted as a binary matrix M(x, y)={0,1}.

Next, one or more digitally reconstructed radiographs (DRRs) may be generated from the acquired 3D model (Step S110). Each DRR is a synthesized 2D projection of the 3D model image data from a particular point of view. Thus, the DRR resembles a 2D X-ray image. As the particular angle of acquisition of the 2D X-ray images may be known to the X-ray imager, this information may be used in render the DRRs from the proper camera angles. However, as the 2D images are acquired intra-operatively in the operating theatre and the 3D image acquisition may be acquired pre-operatively, the pose of the patient may be different between the acquisitions. Accordingly, exemplary embodiments of the present invention seek to apply transformations on the 3D image volume for generating the DRRs to more closely match the intra-operative pose of the patient. As discussed in detail below, this transformation may be a rigid transformation with six degrees of freedom. First an initial approximation of the intra-operative pose of the patient may be used to transform the 3D image and generate the DRRs and thereafter, the pose approximation may be iterated to obtain an optimum match between the DRRs and the respective 2D X-ray images.

As the DRR images rendered from the entire CT volume may include irrelevant structures that would not be visible in the intra-operative subtracted X-ray images, before the DRRs are generated, the abdominal aorta and the iliac arteries may first be segmented from the CT volume, for example, using a graph-cut based segmentation method, as described above. Then, the DDR images may be rendered from the segmented CT volume.

In generating the DRRs, the transformation relating points in the 3D volume to points on the projected image may consist of six extrinsic rigid-body parameters that are estimated by the iterative registration algorithm, and four intrinsic perspective projection parameters that are determined by the X-ray imaging system based on a pinhole camera model. DRRs may be generated using 3-D texture-based volume rendering techniques on graphics processing unit, which may yield a higher degree of computational efficiency than software-based techniques such as ray-casting. It may take, for example, about 15 ms to generate a 256×256 DRR from a 256×256×256 volume using a graphics processing unit (GPU) such as an NVidia Quadro FX 360M.

The DRRs may be generated from a course ROV that is around the spine within the 3D model. The position of the aorta determined during aorta segmentation may be used to obtain the ROV around the spine as the spine is roughly behind abdominal aorta. In particular, with the aorta segmentation mask, the boundary of the bounding box of the aorta may be calculated for each slice and then dilated within the slice to both posterior and left-right directions by a certain size to obtain the spine bounding box. As spine X-ray images from Plane B do not include contrast agent, pixels that belong to the abdominal aorta may be further excluded from the spine segmentation mask.

In addition, to eliminate the artifacts in the DRR images coming from the bounding box, a nonlinear mapping may be performed between the DRR image and the X-ray image within the 2D spine mask M. The nonlinear histogram mapping may be used to align the intensity distribution of DRRs to that of X-ray image which may aid in difference-based similarity measurement.

Figure 2:
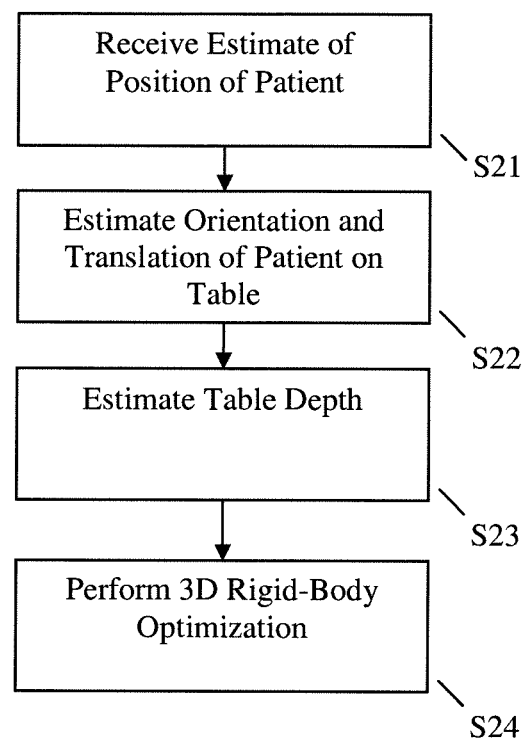
FIG. 2 is a flowchart illustrating an approach for performing 2D/3D registration in accordance with exemplary embodiments of the present invention.

Next, 2D/3D registration may be performed (Step S111). FIG. 2 is a flowchart illustrating an approach for performing 2D/3D registration in accordance with exemplary embodiments of the present invention. Accurate 2D/3D registration may be performed by closely aligning the DRRs with their respective X-ray images. However, as the position of the patient may have changed between the preoperative CT scan of Step S101 and the acquisition of the 2D X-ray images, exemplary embodiments of the present invention seek to compensate for the position of the patient by deforming the CT image to conform to the present pose of the patient.

An initial estimate of the present position of the patient may be received (Step S21), the orientation and translation of the patient on the table plane is estimated (Step S22), the depth of the patient from the table (table depth) is estimated (Step S23), and 3D rigid-body optimization is performed (Step S24). Decoupling of the registration parameters may be based on prior knowledge about the direction of the most dominant patient's motion and typical C-arm angulations used for acquiring the aorta and the spine images.

Exemplary embodiments of the present invention may use a hierarchical intensity-based 2D/3D registration method. Here, the similarity measure may be defined in the aorta image and the spine image separately. Because aorta is shown as a relative large shape, and hence a dominant feature, in both the MO image and the DRR, mutual information (MI) may be a suitable similarity measure as it may be used to compare images from different modalities with large capture range and high accuracy. The similarity of aorta may be defined as mutual information between the DRR image and the MO image in accordance with the formula:

$$S^A(H) = MI(P^A(H \cdot V), I^A) \quad (5)$$

where $P^A$ and $I^A$ are the DRR rendering and the MO image of the aorta. Here $H \cdot V$ is used to denote applying the transformation H on the volume V.

As gradient-based similarity measures may be too suitable for comparing spine images, whose dominant features lie in the edge of the vertebrae, exemplary embodiment of the present invention may utilize a measure of similarity based on gradient differences between the DRR images and the respective X-ray images within the spine mask. Since correlation based method is sensitive to outliers, the sum of the absolute differences of gradients, or Gradient Difference may be used. The similarity for spine image may be defined as Gradient Difference between the DRR image and the X-ray image within the spine mask according to the following equation:

$$S^S(H) = GD(P^S(H \cdot V), I^S, M) \quad (6)$$

where $P^S$ and $I^S$ are the DRR rendering and the X-ray image of the spine, and M is the spine mask discussed above.

The pose of the patient within the CT volume can be represented by six registration parameters, for example: $T = \{x, y, z, \alpha, \beta, \theta\}$, where x, y denote the translation on the table plane, z denotes the position of table depth, and $\alpha$, $\beta$, $\theta$ are rotations about the x, y, z axis. The homogenous transformation matrix of the six parameters may be:

$$H(T) = \begin{bmatrix} 1 & 0 & 0 & x \\ 0 & 1 & 0 & y \\ 0 & 0 & 1 & x \\ 0 & 0 & 0 & 1 \end{bmatrix} \begin{bmatrix} \cos(\theta) & -\sin(\theta) & 0 & 0 \\ \sin(\theta) & \cos(\theta) & 0 & 0 \\ 0 & 0 & 1 & 0 \\ 0 & 0 & 0 & 1 \end{bmatrix} \quad \text{(Equation 9)}$$

$$\begin{bmatrix} \cos(\beta) & 0 & -\sin(\beta) & 0 \\ 0 & 1 & 0 & 0 \\ \sin(\beta) & 0 & \cos(\beta) & 0 \\ 0 & 0 & 0 & 1 \end{bmatrix} \begin{bmatrix} 1 & 0 & 0 & 0 \\ 0 & \cos(\alpha) & -\sin(\alpha) & 0 \\ 0 & \sin(\alpha) & \cos(\alpha) & 0 \\ 0 & 0 & 0 & 1 \end{bmatrix}$$

Based on the prior knowledge of the direction of the most dominant patient's motion and the typical C-Arm angulations used for acquiring the aorta and spine images, the registration parameters to be estimated are the patient's translation and rotation in the table plane, plus the table depth. As the change of table depth has only a subtle impact on the aorta image (AP view) but causes large translation on the projection of spine in the spine image (e.g., 50 degrees apart from AP view), the estimation of table depth can depend solely on spine and may be separated from other parameters. The initial pose estimation may accordingly be focused on estimating the in-table-plane translation x, y.

Estimating the patient's movement on the table plane (Step S22) may be performed prior to estimating the depth of the patient from the table (Step S23) or performing 3D rigid-body optimization (Step S24). This is at least because the patient's movement on the table plane is the least constrained parameter since rotations about the other two axis are relatively constrained, assuming the patient is lying on the table and is in the supine position. Additionally, without correct orientation, it may be very difficult and time consuming to estimate the table depth in the next step because the spine shown in the DRRs could be very different from that in the X-ray image with different orientation and scaling. Also, during AAA interventions the contrast-filled abdominal aorta images are typically taken from roughly AP direction in order to best visualize the aorta/iliac arteries, and the vessels are large and dominant in both DRRs and X-ray images. Therefore patient's movement on the table plane can be well estimated by using the aorta image, and the estimation is not sensitive to the change in the table depth. The spine image need not be used at this step because gradient-based similarity measures may have a relatively small capture range, and when being far away from the correct position the native spine image could bring local minimums that may deteriorate the estimation. In particular, patient's movement on the table plane may be estimated by performing best neighbor optimization starting from the initial position $\{x_0, y_0, 0, 0, 0, 0\}$ to maximize the similarity measure $S^A$, for example, using the equation:

$$\{x_1, y_1, \theta_1\} = \underset{x,y,\theta}{\arg\max} MI(P^A(H(x, y, 0, 0, 0, \theta) \cdot V), I^A) \quad (7)$$

The transformation after estimation of patient's movement on the table may be calculated as:

$$T_1 = \{x_1, y_1, z_0, \alpha_0, \beta_0, \theta_1\} \quad (8)$$

As discussed above, the X-ray spine image may be acquired at an angle of about 40 to 60 degrees apart from the AP view, for example, at 50 degrees. After the rough estimation and compensation of patient's movement on the table plane, the DRRs of the spine may be relatively close to the X-ray spine image in both orientation and scaling, with the mismatch in the table depth being reflected as a translational offset (dominantly in horizontal direction) in the spine projection. Accordingly, in estimating the table depth (Step S33), the translation along the table depth that yields the largest spine similarity measure $S^S$ may be considered to be the correct table depth. For example, the following formula may be used to estimate table depth:

$$\{y_2, z_2\} = \underset{y,z}{\arg\max} GD(P^S(H(x_1, y, z, \alpha_0, \beta_0, \theta_1) \cdot V), I^S, M) \quad (9)$$

Here the table depth may be globally searched, for example, in the range of [−20 mm, 20 mm], with fine tuning of the translation in the head-foot (HF) direction in the range of [−5 mm, 5 mm]. Fine tuning of the translation in the HF direction may be performed to overcome a slight panning effect due to perspective projection. A global search may be performed because gradient-based similarity measures typically have a sharp peak but with a very small capture range. By decoupling of the registration parameters in the above two steps, the aorta and the spine images are utilized for robust and efficient coarse alignment of the volume in 3D without introducing any complications such as the weighting of the two types of similarity measures, MI and GD. The transformation after estimation of the table depth may be denoted as:

$$T^2 = \{x_1, y_2, z_2, \alpha_0, \beta_0, \theta_1\} \quad (10)$$

Rigid body registration (Step S24) may be performed starting from the estimated orientation and translation. Accordingly, rigid-body registration may be performed as the last step of a hierarchical registration scheme. An accurate registration of the abdominal aorta (the target organ) may be achieved using the spine as a reliable constraint in 3D. Difficulty may derive from the different nature of the two X-ray images and the potential discrepancy due to the relative movement between the spine and the aorta. To this end, exemplary embodiments of the present invention utilize a two-stage registration strategy. First, a rigid-body fine tuning of the spine is performed by maximizing $SM_{spine}$ using the best neighbor optimizer, with the resulted position denoted by $T^3$. This registration may be performed within a relatively constrained 3D space centered on the coarse alignment position $T^2$, and accordingly, the volume position may remain relatively correct in 3D after this step. An accurate alignment of the spine in the spine imaging plane may result and this alignment may be used for 2D back-projection error quantification of the spine in the second stage of the rigid-body registration.

In the second stage of the rigid-body registration, six anchor points $q^i$, $l=1, \ldots, 6$ in 3D may be uniformly sampled from the segmented spine, and the rigid-body transformation space may be randomly sampled to obtain 50 valid positions where the average 2D back-projection error of the six anchor points onto the spine image are smaller than a predetermined threshold which may be, for example, 5 mm. This randomized sampling can be performed efficiently because DRR generation is not needed. Moreover, the capture range of registration may be increased by sampling the non-convex space within a particular 2D projection error. Possible discrepancies between the two views coming from the relative movement of the organs and/or calibration inaccuracy may also be present. The first twenty positions that yield the largest aorta similarity measure $SM_{aorta}$ may be selected and ten additional poses may be further randomly sampled in the neighborhood of each of the twenty positions. A best neighbor optimization may be finally performed starting from the position among the two hundred candidates with the largest similarity measure of the aorta, and the final registration may be obtained as:

$$T^4 = \underset{T}{\arg\max} MI(P^A(H(T) \cdot V, I^A)) \quad (11)$$

$$\text{s.t.} \sum_{i=1}^{6} \|H^S(H(T) \cdot q^i) - H^S(H(T^3) \cdot q^i)\|_2 < \sigma$$

where $H^S$ is the projection matrix for the spine image, $H^S(H(T) \cdot q^i)$ is the 2-D projection of the i-th anchor point onto the spine X-ray image with transformation T, and $\sigma=5$ mm the threshold on the 2-D back-projection error of the spine quantified using the selected anchor points.

In this way, a first DRR rendered from the CT image may be matched to the MO image derived from the Plane A X-rays by way of minimizing gradient differences between the abdominal aorta in each image. Similarly, a second DRR rendered from the CT image may be matched to the native Plane B X-ray image, which is acquired without visible contrast, by way of minimizing gradient differences between the spine in each image. The DRRs may be re-rendered to achieve optimal pose as the gradient differences are minimized. The final anatomical relationship between the DRRs and the corresponding 2D images may then be used to establish the 2D/3D registration in Step S114. Thereafter, continued 2D fluoroscope images may be registered to the 3D model using the established 2D/3D registration (Step S112). Accordingly, real-time visualization may be achieved and this visualization may be used to provide guidance during intervention such as AAA (Step S113).

Figure 3:
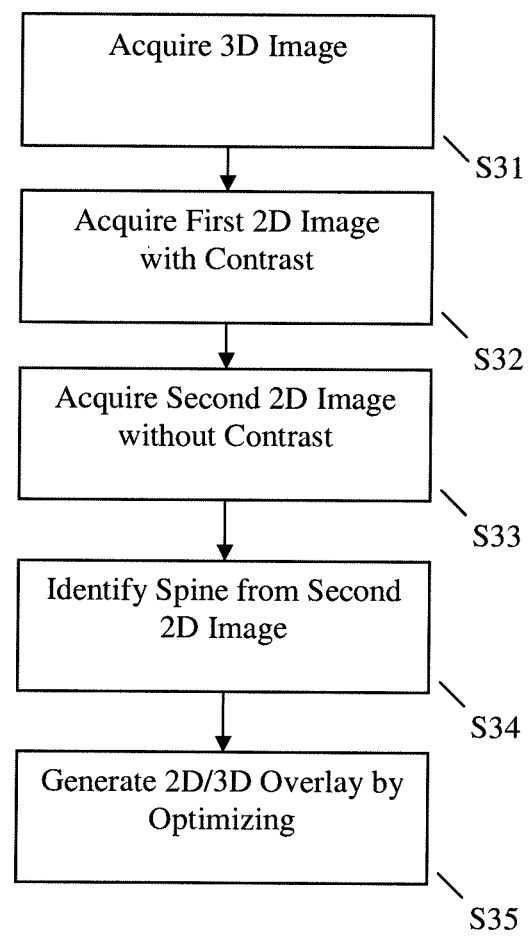
FIG. 3 is a is a flowchart illustrating an approach for performing 2D/3D registration in accordance with exemplary embodiments of the present invention.

While the exemplary approach discussed above with respect to FIG. 1 describes many steps, not all steps so described are necessary for practicing exemplary embodiments of the present invention. FIG. 3 is a flowchart illustrating an approach for performing 2D/3D registration in accordance with exemplary embodiments of the present invention.

First, a 3D image of a patient may be acquired (Step S31). The 3D image, as discussed above, may be a CT scan of the patient. Then, a first 2D image of the patient may be acquired with contrast (Step S32). The 2D image may be an X-ray image taken at a first angle and may clearly show the aorta, for example, as made visible (or otherwise identifiable) by the contrast. Thereafter, a second 2D image of the patient may be acquired (Step S33). The second 2D image may also be an X-ray image. This image may be taken at a different angle than that of the first 2D image. The second 2D image may be acquired without the use of contrast. The spine may be visible (or otherwise identifiable) within the second 2D image. As the second 2D image may be acquire without the use of contrast, the aorta might not be identifiable from this image. Moreover, even though the second 2D image may be acquired after the acquisition of the first 2D image (although this is not a requirement), the contrast administered for the acquisition of the first 2D image would be substantially cleared from the patient at the time of the acquisition of the second 2D image.

The spine may be identified from the second 2D image (Step S34). Both the aorta and spine may be identifiable from the 3D image.

A 2D/3D overlay may then be generated (Step S35). The overlay is an association between the coordinate systems of the 2D image and the 3D image and can, once generated, be used to bring subsequently acquired 2D images into the 3D coordinate system or can be used for a wide range of other purposes. The 2D/3D overlay may be generated by optimizing a measure of similarity between the first 2D image and the 3D image based on the aorta and by optimizing measure of similarity between the second 2D image and the 3D image based on the spine. Optimizing these similarity measures may include refining an approximation of a pose of the patient within the 3D image so that the 3D image may be corrected for changes in the pose of the patient that occur in the time between the 3D acquisition and the 2D acquisitions.

Figure 4:
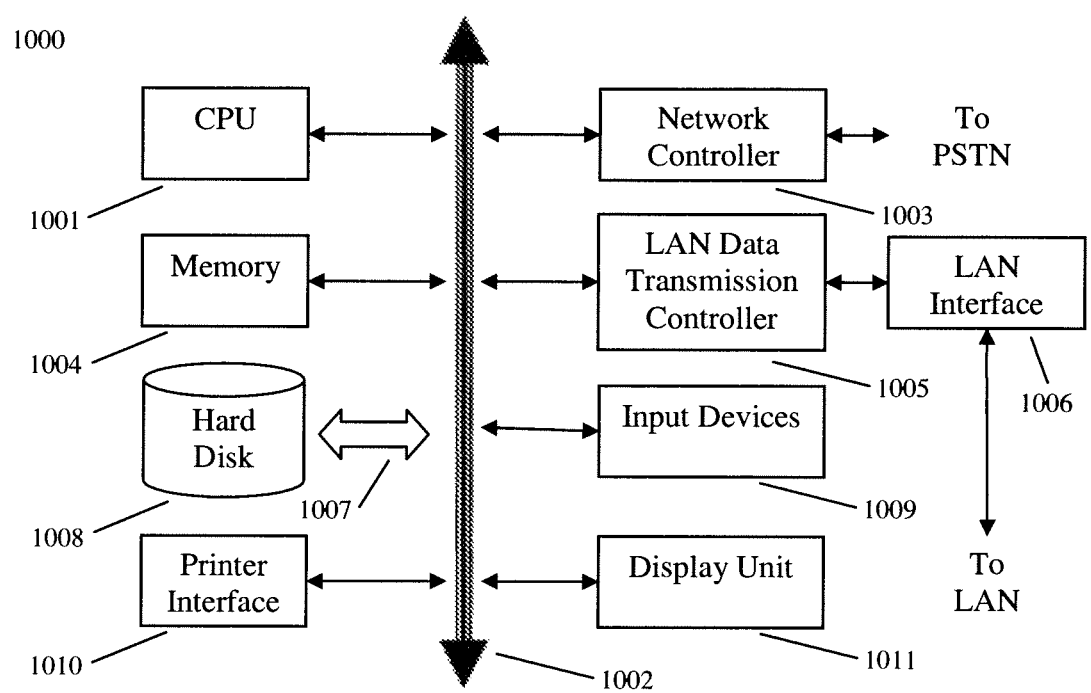
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for performing 2D/3D registration, comprising:
    acquiring a pre-operative 3D image of a patient;
    acquiring an intra-operative pre-contrast 2D image of the patient from a first view;
    administering a radiocontrast agent to the patient;
    acquiring a sequence of intra-operative post-contrast 2D images of the patient from the first view;
    acquiring an intra-operative 2D image of the patient from a second view that is acquired at a different angle with respect to the patient than the first view;
    subtracting the first view pre-contrast 2D image from each of the first view post-contrast 2D images to produce a set of first view subtraction images;
    generating a maximum opacity (MO) image from the set of first view subtraction images;
    generating a first synthetic 2D view from the pre-operative 3D image that approximates the first view based on an initial approximation of an intra-operative pose of the patient;
    generating a second synthetic 2D view from the pre-operative 3D image that approximates the second view based on the initial approximation of the intra-operative pose of the patient; and
    generating a 2D/3D registration result by optimizing a measure of similarity between the first synthetic 2D view and the MO image and a measure of similarity between the second synthetic image and the intra-operative 2D image of the patient from the second view by iteratively adjusting the approximation of the pose of the patient and iterating the first and second synthetic 2D views using the adjusted approximation of the pose of the patient.

2. The method of claim 1, further comprising:
    acquiring real-time 2D images of the patient; and
    using the generated 2D/3D registration result to register subsequent 2D images to the 3D image.

3. The method of claim 1, wherein the measure of similarity between the first synthetic 2D view and the MO image is bases on visualization of an aorta and the measure of similarity between the second synthetic 2D view and the intra-operative 2D image of the patient from the second view is based on visualization of a spine.

4. The method of claim 1, wherein optimizing a measure of similarity between the first synthetic 2D view and the MO image and a measure of similarity between the second synthetic 2D image and the intra-operative 2D image of the patient from the second view includes:
   estimating an on-table-plane translation and rotation by optimizing Euclidean transformation parameters to maximize a measure of similarity between the first synthetic 2D view and the MO image;
   estimating a table depth by maximizing a measure of similarity between the second synthetic 2D image and the intra-operative 2D image of the patient from the second view by local exhaust search;
   refining the table depth by optimizing the Euclidean transformation parameters to maximize a measure of similarity between the second synthetic 2D image and the intra-operative 2D image of the patient from the second view;
   refining an abdominal 2D/3D overlay by optimizing Euclidean transformation parameters to maximize a measure of similarity between the first synthetic 2D view and the MO image while keep a 2D/3D overlay of spine in the second view unaffected; and
   using a final pose yielded by a final pose refining procedure as a 2D/3D registration result.

5. The method of claim 4, wherein:
   the Euclidean transformation parameters optimized in estimating the on-table-plane translation and rotation include two dimensions of in-table-plane translation and one dimension of in-table-plane rotation; and
   the local exhaust search is performed in two directions: head-foot, and table depth.

6. The method of claim 1, wherein the pre-operative 3D image is manually bridged into 15 mm capture range of a target position.

7. The method of claim 1, wherein there is no observable contrast in the intra-operative 2D image of the patient from the second view.

8. The method of claim 1, wherein the pre-operative 3D image is a computed tomography (CT) scan.

9. The method of claim 1, wherein the first view is an anteroposterior view.

10. The method of claim 1, wherein the second view is acquired at an angle that differs from the angle of the first view by 20 to 160 degrees.

11. The method of claim 1, wherein the second view is acquired at an angle that differs from the angle of the first view by 40 to 60 degrees.

12. The method of claim 1, wherein the second view is acquired at an angle that differs from the angle of the first view by 50 degrees.

13. The method of claim 1, wherein the intra-operative pre-contrast 2D image, the sequence of intra-operative post-contrast 2D images of the patient from the first view, and the intra-operative 2D image of the patient from a second view are all X-ray images.

14. The method of claim 1, wherein the intra-operative pre-contrast 2D image, the sequence of intra-operative post-contrast 2D images of the patient from the first view, and the intra-operative 2D image of the patient from a second view are acquired using an X-ray imager mounted to a C-arm, the angle of which is changed from the angle of the first view to the angle of the second view between the acquisition of the sequence of intra-operative post-contrast 2D images of the patient from the first view and the acquisition of the intra-operative 2D image of the patient from a second view.

15. The method of claim 1, wherein subtracting the first view pre-contrast 2D image from each of the first view post-contrast 2D images to produce a set of first view subtraction images includes performing digital subtracted angiography (DSA).

16. The method of claim 1, wherein generating the MO image from the set of first view subtraction images includes generating a composite image in which each pixel of the composite image is taken as a corresponding pixel having a maximum opacity out of among the first view subtraction images.

17. The method of claim 1, wherein generating the MO image from the set of first view subtraction images includes performing an anisotropic diffusion process.

18. The method of claim 1, wherein the spine is segmented from the intra-operative 2D image of the patient from a second view.

19. A method for performing 2D/3D registration, comprising:
   acquiring a pre-operative 3D image of a patient;
   acquiring a first intra-operative 2D image of the patient from a first view using contrast;
   acquiring a second intra-operative 2D image of the patient from a second view without using contrast, wherein the second view is at a different angle with respect to the patient than the first view;
   generating a first synthetic 2D view from the pre-operative 3D image that approximates the first view based on an initial approximation of an intra-operative pose of the patient;
   generating a second synthetic 2D view from the pre-operative 3D image that approximates the second view based on the initial approximation of the intra-operative pose of the patient;
   optimizing a measure of similarity between the first synthetic 2D view and the first intra-operative 2D image and a measure of similarity between the second synthetic image and the second intra-operative 2D image by iteratively adjusting the approximation of the pose of the patient and iterating the first and second synthetic 2D views using the adjusted approximation of the pose of the patient; and
   using the final iteration of the first and second synthetic 2D views to register subsequent 2D images to the 3D image.

20. A method for performing 2D/3D registration, comprising:
   acquiring a 3D image of a patient;
   acquiring a first 2D image of the patient with contrast;
   acquiring a second 2D image without contrast;
   identifying a spine from the second 2D image of the patient;
   generating a 2D/3D overlay by optimizing a measure of similarity between the first 2D image and the 3D image based on the aorta and by optimizing a measure of similarity between the second 2D image and the 3D image based on the spine.

21. The method of claim 20, wherein optimizing the measure of similarity between the first 2D image and the 3D image includes:
   estimating an on-table-plane translation and rotation by optimizing Euclidean transformation parameters to maximize a measure of similarity between the first 2D image and a first synthetic image of the 3D image;

estimating the table depth by optimizing the Euclidean transformation parameters to maximize a measure of similarity between the second 2D image and the second synthetic image of the 3D image;

refining the 2D/3D overlay by optimizing Euclidean transformation parameters to maximize a measure of similarity between the first 2D image and the first synthetic image of the 3D image; and using a final pose yielded by a final pose refining procedure as a 2D/3D registration result.

* * * * *